(12) United States Patent
Phillips

(10) Patent No.: US 7,871,416 B2
(45) Date of Patent: Jan. 18, 2011

(54) CLAMP DEVICE TO PLICATE THE STOMACH

(76) Inventor: Edward H. Phillips, 712 N. Roxbury Dr., Beverly Hills, CA (US) 90210

( * ) Notice: Subject to any disclaimer, the term of this patent is extended or adjusted under 35 U.S.C. 154(b) by 1579 days.

(21) Appl. No.: 11/188,070

(22) Filed: Jul. 22, 2005

(65) Prior Publication Data

US 2007/0021761 A1  Jan. 25, 2007

(51) Int. Cl.
*A61B 17/08* (2006.01)
(52) U.S. Cl. .................. 606/151; 606/157; 600/37
(58) Field of Classification Search .............. 606/157, 606/158, 151, 152, 153, 154, 155, 156, 201, 606/202; 623/23.65; 600/29–32, 37, 207
See application file for complete search history.

(56) References Cited

U.S. PATENT DOCUMENTS 4,586,501 A    5/1986  Claracq 5,236,437 A *  8/1993  Wilk et al. .................. 606/207
5,601,604 A    2/1997  Vincent

OTHER PUBLICATIONS

PCT Pub. No. WO01/24742, Bruno Longobardi, Adjustable Gastric Implant, Apr. 21, 2001, Entire document.*

* cited by examiner

*Primary Examiner*—Anhtuan T Nguyen
*Assistant Examiner*—Tuan V Nguyen
(74) *Attorney, Agent, or Firm*—Frederick Gotha

(57) ABSTRACT

A medical device for clamping the stomach in morbid obesity surgery consists of a silicone frame that is essentially U-shaped, having opposing legs self-hinged to a bight portion interconnecting the legs. The opposing legs have sufficient stiffness to permit limited bending and have inner surfaces that sealingly carry an inflatable balloon which can be selectively inflated or aspirated after the device has been clamped to the stomach to adjust the gastric restriction stoma. A flexible latch member carried by one of the legs has at least one serration which is inserted into a latch cavity of the opposing leg to lock the opposing legs in fixed spaced relationship. Lumens within the legs communicate with a fluid supply source and respective inflatable balloon for selective inflation or aspiration of the inflatable balloons.

5 Claims, 5 Drawing Sheets

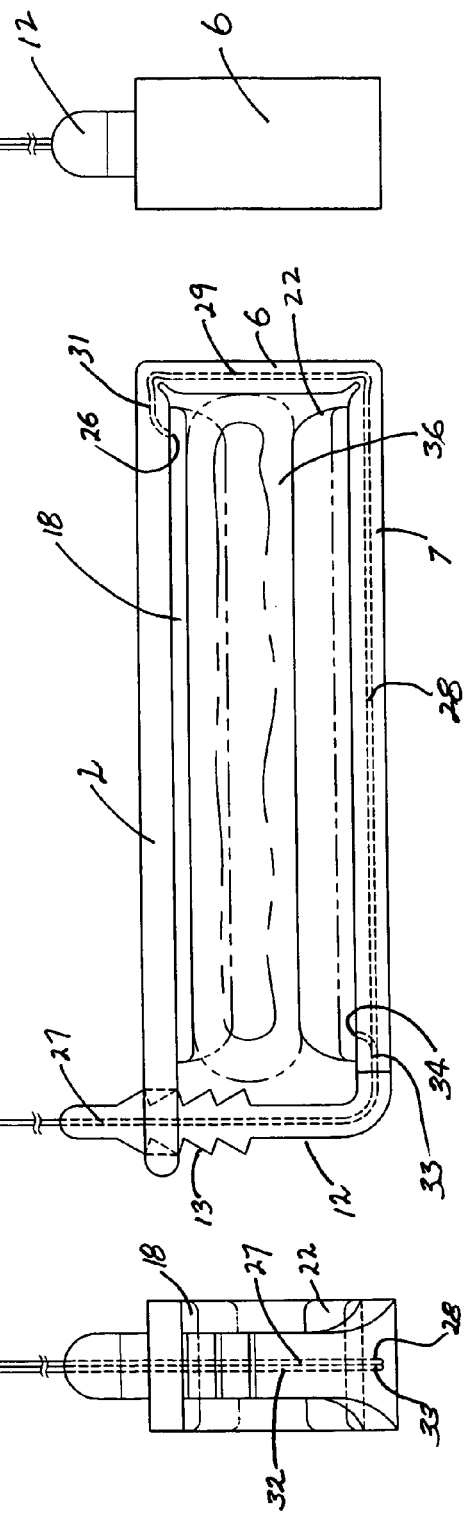
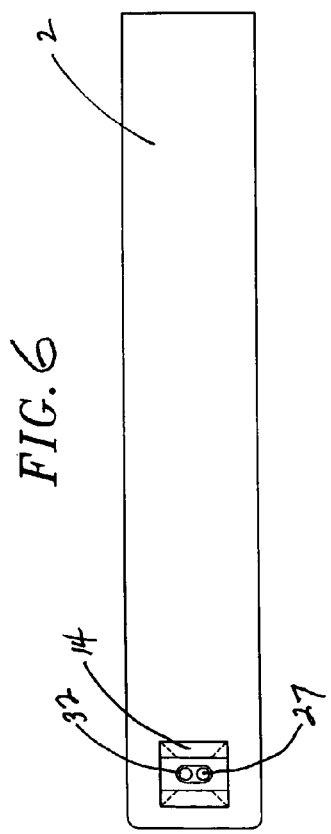

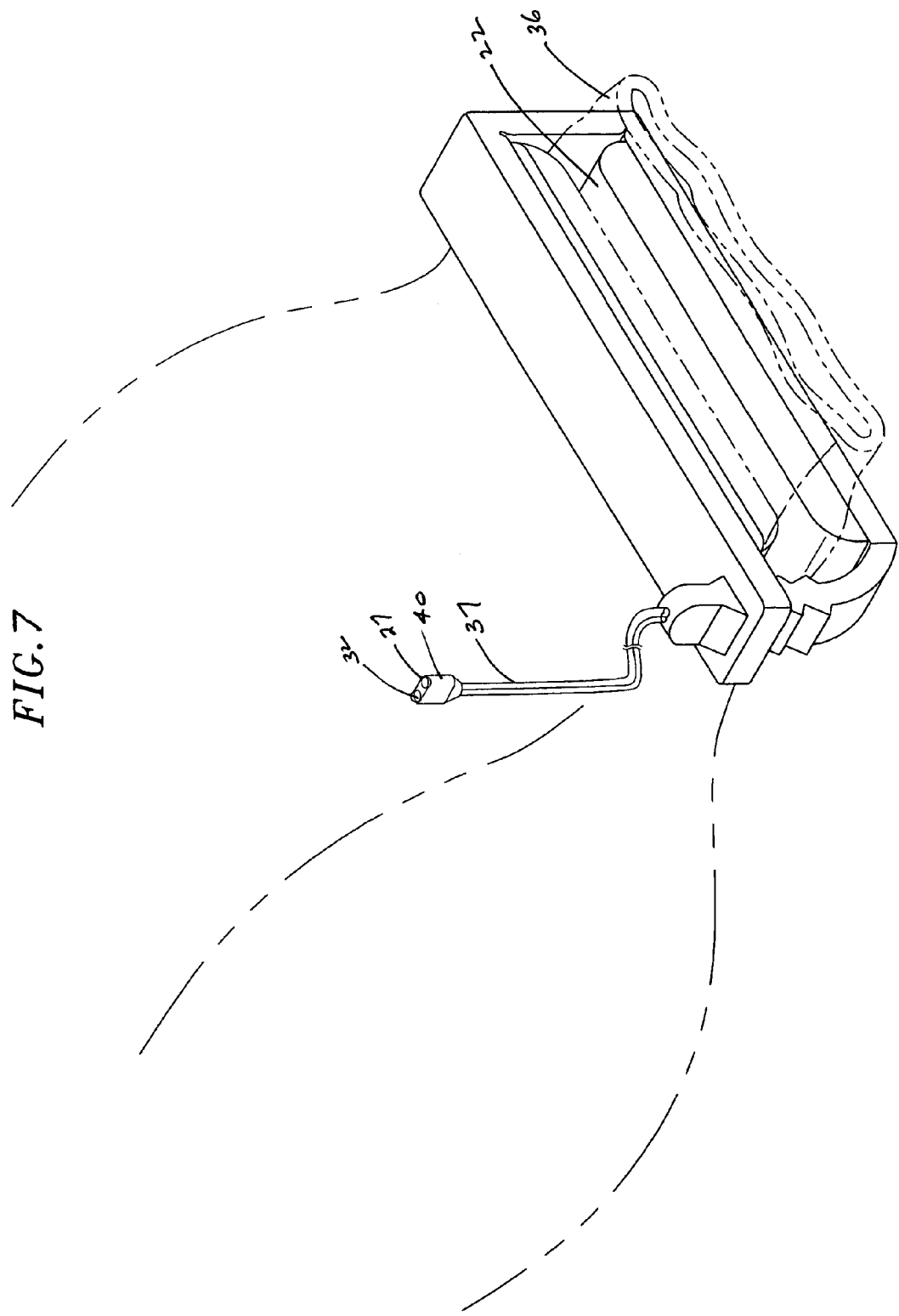

CLAMP DEVICE TO PLICATE THE STOMACH

FIELD OF THE INVENTION

This invention relates to a medical device for clamping the stomach in morbid obesity bariatric surgery.

BACKGROUND OF THE INVENTION

One of the most common illnesses is obesity. Many diseases are caused by or exacerbated by obesity, particularly in the western world, and these illnesses may be accompanied by physical and psychological disabilities. Surgical methods for controlling weight initially involved gastric stapling in various forms, which, over a prolonged period, resulted in major weight reduction. Because of the invasiveness of this type of surgery, and the irreversibility of it, the gastric stapling surgical technique was not widely accepted. These surgical procedures required a laparotomy which carried the risk of morbidity and death. Additionally, the gastric stapling technique required that the setting of the gastric restriction be initially set correctly because of the inability of the surgeon to modify the degree of restriction after the operation was performed. To overcome this difficulty, adjustable gastric banding was introduced which utilized an inflatable balloon carried by a band that could be placed around the stomach by an open operation or laparoscopically. The later technique has become the preferred surgical technique because of the reduced invasiveness of the operation. The degree of gastric restriction after placement of the band around the stomach immediately below the oseophagogastric junction was controlled by inflating an encircling balloon which was sealingly carried on the inner surface of the band; however, the bands of the prior art created the gastric restriction by annularly or hoop compressing the stomach. A possible consequence of annular stress is the inducement of erosion that permitted the band to go into the bowel thereby causing bleeding, infection, and even death. Thus, it is desirable to provide a stomach plication device that avoids annular stress, that utilizes inflatable members to prolong the life of the plication device, that is laparoscopically implantable, avoids erosion, and is adjustable to control the gastric restriction stoma after the operation is completed.

SUMMARY OF THE INVENTION

There is, therefore, provided according to the present invention a fluid inflatable clamp device to plicate the stomach for morbid obesity surgery and substantially reduce the risk of band erosion resulting form annular compression of the stomach. The inflatable device is adjustable and can be placed laparoscopically or by open operation.

The present invention is directed to embodiments that utilize opposing legs carrying an inflatable balloon member in one embodiment or balloons in other embodiments to permit clamping of the stomach below the grastroesphogeal junction. By selectively inflating or aspirating opposing balloons, the life of the clamp may be substantially prolonged and consequently the frequency of replacement surgery greatly reduced. The device is preferably made of silicone where the legs are so constructed and proportioned to have sufficient stiffness to permit limited bending and are so hinged such that the hinged ends of the legs are in fixed lateral spaced relationship.

In each of the embodiments of the invention, the fluid inflatable device to plicate the stomach is U-shaped and consists of a first leg or plate having a preferably rectangular shape where the first leg has a free first end and a hinged opposite end and an axis of elongation; a second leg having substantially the same configuration as the first leg also has a hinged end and free second end. The hinged ends of the legs are integrally connected to a laterally extending bight portion which has sufficient stiffness to retain the legs in fixed lateral spaced relationship at their hinged ends.

In the preferred embodiment, the first leg has a first lumen extending at least in part axially therein that communicates with a first inflation port and, likewise, the second leg has a second lumen extending at least in part axially therein that communicates with a second inflation port. However the second leg also has a third lumen extending axially therein that communicates with a bight lumen extending laterally through the bight portion where the bight lumen is in fluid communication with the first lumen. Thus, a flow path is provided that permits fluid flow for inflating or aspirating a first inflatable member that is peripherally sealed and extends axially along the inner surface of the first leg. A separate flow path is provided to permit fluid flow through the second lumen and second inflation port for inflating and aspirating a second inflatable member that is peripherally sealed and extends axially along the inner surface of the second leg; the second inflatable member is oppositely positioned from the first inflatable member when the stomach is clamped.

The embodiment above described further includes latch means associated with the first and second legs at their free ends to permit the legs to be locked in pre-determined fixed lateral relationship during the clamping of the stomach. Separate fluid flow paths are defined by first and second conduits which are contained within a flexible latch member having at least one serration where the flexible latch member is integrally carried by the second leg member adjacent its free end; the first conduit of the flexible latch member communicates with the second lumen and the second conduit of the flexible latch member communicates with the third lumen. Fluid supply means associated with the latch means permits saline fluid to be selectively supplied or aspirated through the first conduit to inflate or aspirate the first inflatable member to a pre-determined pressure. The second inflatable member may be separately inflated to a pre-determined pressure by the fluid supply means supplying or aspirating fluid through the second conduit of the flexible latch member. To secure the free ends of the first and second legs in substantially fixed lateral spaced relationship, the first leg has a latch cavity adjacent the free end so dimensioned and proportioned to permit locking engagement with a selected serration of the serrated flexible latch member.

In another embodiment of this invention, the inflatable device has as in the preferred embodiment a first leg, preferably of plate shape, an axis of elongation, a first end and a hinged end, a first inflation port, and a first lumen extending at least in part axially therein; a second leg having substantially the same rectangular plate configuration as the first leg, an axis of elongation, a hinged end, a free end, and a second lumen extending at least in part axially therein where the second lumen communicates with a second inflation port. The hinged ends of the legs are self hinged and integrally associated with a laterally extending bight portion where the bight portion has sufficient stiffness to retain the legs in fixed lateral spaced relationship at their hinged ends. The bight portion contains a laterally extending bight lumen that communicates with the first and second lumens thereby providing a fluid flow path to the first inflation port. The first inflatable member which is sealingly carried by the first leg extends at least in part axially on the inner surface of the first leg where the first inflatable member communicates with the first inflatable port. The second leg sealingly carries a second inflatable member which is oppositely positioned from the first inflatable member when the stomach is clamped between the first and second legs. As in the preferred embodiment above described, in this embodiment the serrated flexible latch member is carried by the second leg adjacent its free end and the flexible latch member contains a first conduit therein in fluid communication with the second lumen. To secure the free ends of the first and second legs in fixed space relationship, the first leg has a latch cavity adjacent to the free end that is so dimensioned and proportioned to permit locking engagement with a selected serration of the serrated flexible latch member. A fluid supply and aspiration means is associated with the serrated flexible latch member and communicates with the first conduit to selectively permit inflation or aspiration of both the first and second inflatable members.

In yet still another embodiment, the plication device is of similar construction as in the previous embodiments. As in the above described embodiments, the plication device is preferably U-shaped and has a first leg and a second leg which are preferably of a rectangular plate shape and self-hinged to the bight portion so as to permit the legs to articulate with respect to the bight portion. An axis of elongation extends through the first leg, bight portion, and second leg and a single inflatable member is sealingly carried and extends axially and continuously on the inner side of the first and second legs and bight portion. The first leg has a first lumen that communicates with an inflation port that is in fluid communication with the single inflatable member. As in the above described embodiments, a flexible latch member is associated with the first and second legs for spacing the legs in substantially fixed spatial relationship where the flexible latch member contains at least one serration. The flexible latch member has a first conduit therein that is in fluid communication with the first lumen. A fluid supply means, as described in the above embodiments, is associated with the flexible latch member for selectively supplying and aspirating fluid through the first conduit to inflate or aspirate the inflatable member to a pre-determined pressure or lateral distance from the inner surfaces of the first and second legs

BRIEF DESCRIPTION OF THE DRAWINGS

These and other features and advantages will become appreciated as the same become better understood with reference to the following specification, claims and drawings wherein:

FIG. 3 is a side view of FIG. 1 illustrating the preferred embodiment of this invention in a latched configuration with the stomach plicated.

FIG. 4 is a front view of FIG. 3.

FIG. 5 is a rear view of FIG. 3.

FIG. 6 is a top view of FIG. 3.

FIG. 7 is a perspective view of the preferred embodiment illustrating the device in latched configuration with the stomach plicated.

DETAILED DESCRIPTION

Figure 1:
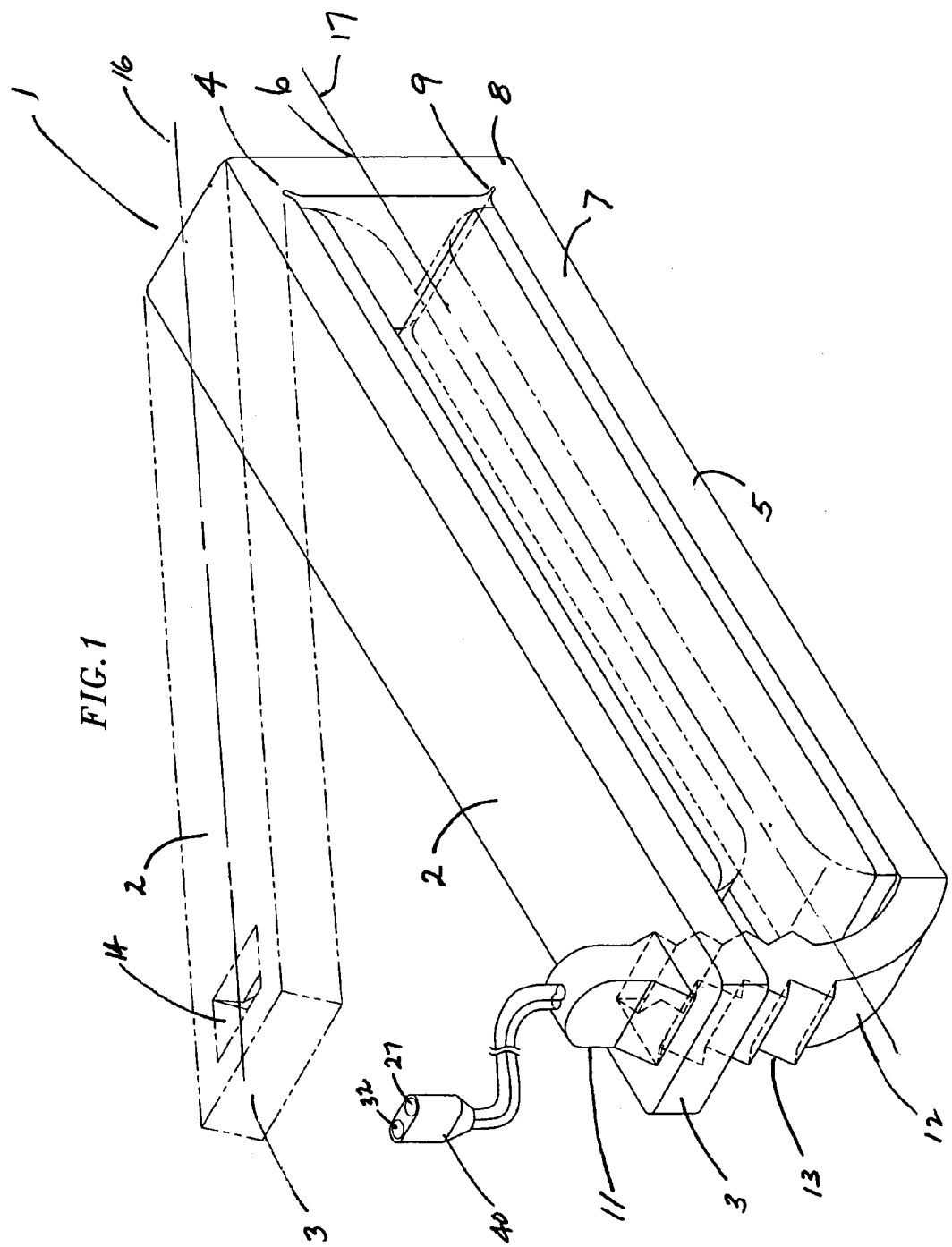
FIG. 1 is a perspective view of the preferred embodiment of the stomach plication device of this invention for morbid obesity surgery illustrating the device open and latched configurations.

FIG. 1 is a perspective of the preferred embodiment illustrating the stomach plication device 1 of this invention in both latched and unlatched configurations. As can be seen in FIG. 1, the first leg 2 is shown in phantom to depict the unlatched configuration; and the latched, closed configuration, is shown in solid lines. In the preferred embodiment the frame 5 of plication device 1 is U-shaped having a pair of opposing legs or rectangular plates interconnected by a bight and made of a silicone material. The frame consists of first leg or rectangular plate 2 which has a free-end 3 and a hinged-end 4. Hinged-end 4 is integrally connected and self-hinged to bight portion 6. First leg 2 is so constructed and proportioned to have sufficient stiffness to permit limited bending and to have sufficient flexibility at the juncture of the first leg and bight portion to rotate with respect to bight portion 6 at its hinged end 4. Bight portion 6 is also shaped rectangularly and is preferably made of a stiff silicone material with sufficient flexibility at the juncture of second leg 7 and bight portion 6 so as to form self-hinging joint 8; bight portion 6 is of sufficient stiffness such that the lateral distance between the hinged end 4 of first leg 2 and hinged end 9 of second leg 7 is essentially constant.

Figure 2:
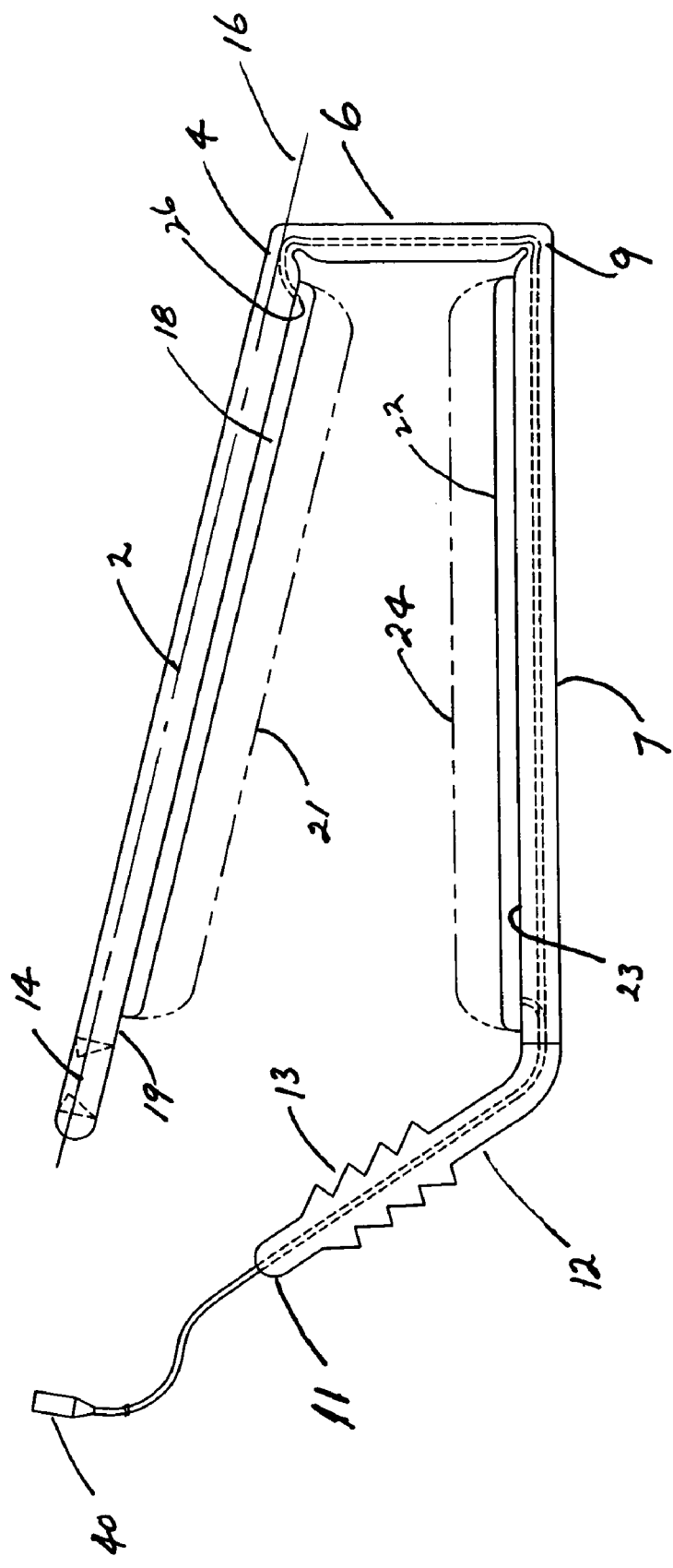
FIG. 2 is a side view of FIG. 1 illustrating the preferred embodiment in the unlatched open configuration.
Figure 10:
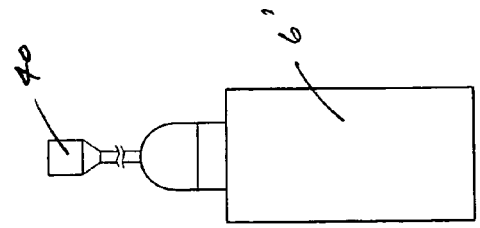
FIG. 10 is a rear view of FIG. 8.

Referring to FIGS. 1 and 2, it can be seen that second leg 7 has a free-end portion 11 that contains flexible latch member 12 which is bendable with respect to second leg 7 and consists of a multiplicity of serrations 13 to permit the forming of an adjustable latch lock with first leg 2. To form the latch lock, the serrations 13 are sequentially advanced through latch cavity 14 until a desired lateral separation between first leg 2 and second leg 7 is achieved. Each of the serrations 13 and latch cavity 14 are so dimensioned and constructed such that when a serration sufficiently engages latch cavity 14, the serration cannot be withdrawn back through the latch cavity.

Referring again to FIGS. 1 and 2, it can be seen that, first leg 2 has an axis of elongation 16 and second leg 7 has an axis of elongation 17. First inflatable member 18 is carried by first leg 2 and extends axially along inner surface 19 of the first leg. First inflatable member 18 is peripherally sealed to inner surface 19 and is selectively inflatable, preferably with saline fluid, to a desired lateral distance from inner surface 19 such as that illustrated in FIG. 2 by phantom line 21. In a like manner, second inflatable member 22 is peripherally sealed to inner surface 23 and extends axially along inner surface 23 of second leg 7 and is selectively inflatable with a saline fluid to a desired lateral dimension as illustrated in FIG. 2 by phantom line 24. In the preferred embodiment, first and second inflatable members are separately inflatable as hereafter described by reference to FIGS. 3, 4, 5, and 6.

As can be seen is FIG. 3, the stomach 36 is plicated between first leg 2 and second leg 7 by inflation of second inflatable member 22. First inflatable member 18 as shown in FIG. 3 has not been inflated while second inflatable member 22 is inflated to illustrate that either inflatable member or both can be used to further plicate the stomach 36 between the first and second legs.

The flow paths for inflating and aspirating inflatable members 18 and 22, and the corresponding inflation ports, can be seen by reference to FIG. 3. First leg 2 has a first inflation port 26 that communicates with first inflation member 18. Saline fluid for inflating first inflation member 18 is supplied from reservoir 40 through first conduit 27 that extends axially within flexible latch member 12 and communicates with third lumen 28. A fluid flow path is provided to first inflation port 26 by third lumen 28 which extends axially within and through second leg 7 and communicates with bight lumen 29. Bight lumen 29 extends laterally through bight portion 6 and in turn communicates with first lumen 31; first lumen 31 extends in part axially within first leg 2 completing the flow path to first inflation port 26. To inflate second inflatable member 22, a separate flow path is provided through second conduit 32 which extends axially through flexible latch member 12 and communicates with second lumen 33; second lumen 33 extends at least in part axially within second leg 7 and communicates with second inflation port 34. Thus, saline fluid may be separately supplied to inflate or aspirate second inflatable member 22 to a desired lateral dimension.

Referring now to FIG. 7, which is a perspective view of the preferred embodiment, stomach 36 is shown to be plicated between first leg 2 and second leg 7 with second inflatable member 22 sufficiently inflated to define a gastric restriction stoma. Although not shown in the drawings, a reservoir 40 is implanted in the patient and contains saline. Reservoir 40 communicates with conduits 27 and 32 which are contained within silicon tubing 37. Reservoir 40 is implanted during the operation within the left rectal muscle bed. The use of a silicone implanted reservoir to supply saline to inflate or aspirate a balloon is well known in the prior art and widely used in lap band gastric surgical procedures. The reservoir is attached to the anterior rectal sheath by absorbable sutures. After the operation is completed, the gastric restriction stoma can be modified according to a patient's need. This is accomplished by use of a needle selectively inserted into injection ports carried by the reservoir. The reservoir has two injection ports located under the skin which can be localized radioscopically; the needle is then introduced into a respective port to inflate or aspirate the inflatable member communicating with that port. The preferred embodiment permits the surgeon after the plicating device has plicated the stomach to selectively inflate or aspirate either or both inflatable members to modify the gastric restriction stoma.

Figure 11:
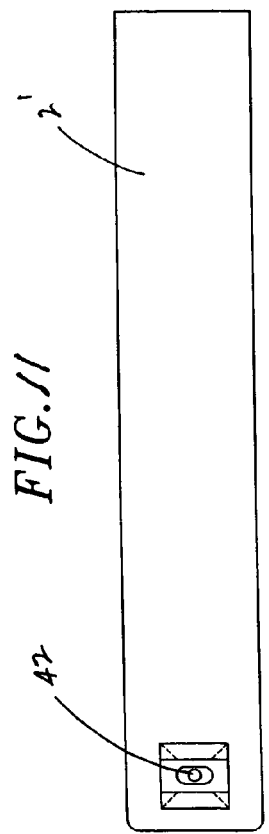
FIG. 11 is a top view of FIG. 8.
Figure 8:
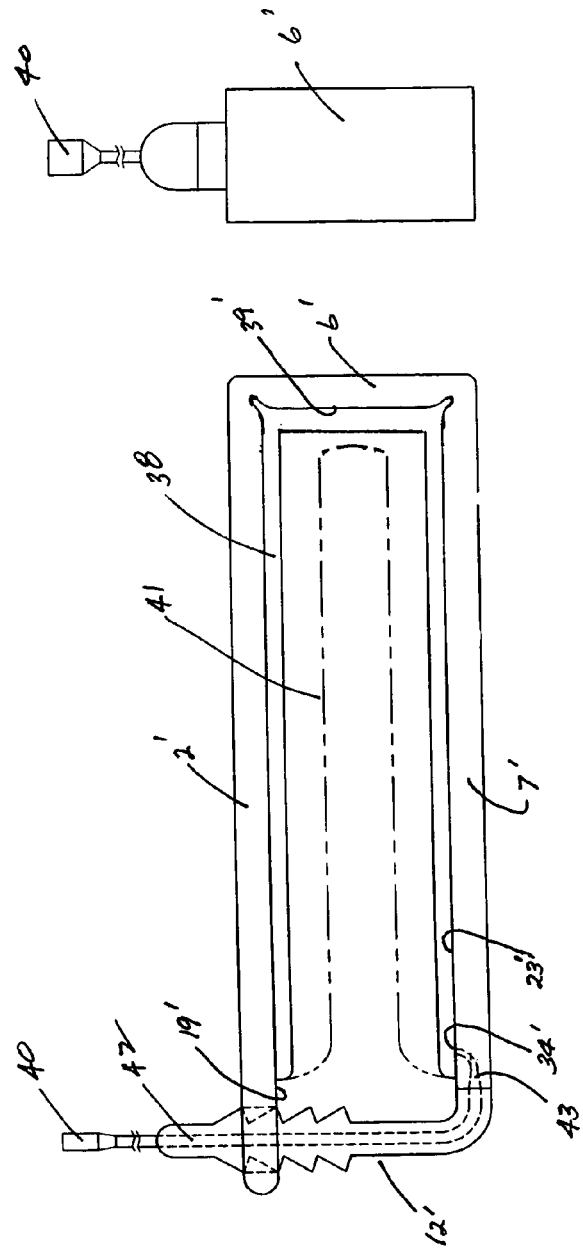
FIG. 8 is a side view of another embodiment of this invention.
Figure 9:
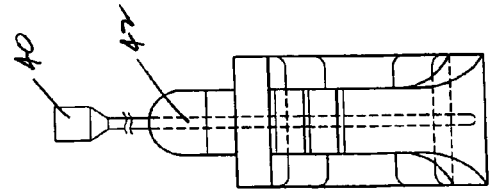
FIG. 9 is a front view of FIG. 8.

Another embodiment of this invention is illustrated in FIGS. 8, 9, 10, and 11. The basic distinction between this embodiment and the preferred embodiment described above is that a single inflatable member 38, shown in FIG. 8, is utilized rather than two separately inflatable members. By referring to FIG. 8, it can be seen that inflatable member 38 extends axially along the inner surface 19' of first leg 2', laterally along the inner surface 39 of bight portion 6', and axially along the inner surface 23' of second leg 7'. Single inflatable member 38 is peripherally sealed to the inner surfaces of first leg 2', bight portion 6', and second leg 7'; the expansion of single inflatable member 38 upon inflation is shown in FIG. 8 by phantom line 41. Inflation and aspiration of single inflatable member 38 is illustrated by reference to FIGS. 8, 9, and 11. As can be seen in FIG. 11, a single conduit 42 extends within and through flexible latch member 12' and as shown in FIG. 8 communicates with lumen 43 which extends at least in part axially within second leg 7' and communicates with inflation port 34'. Although not shown, a saline reservoir is implanted in the patient and communicates with conduit 42 to supply and aspirate saline to and from single inflatable member 38. As described above in the description of the preferred embodiment, the use of a silicone implanted reservoir 40 to supply saline to inflate or aspirate a balloon in lap band gastric surgery is well known. The reservoir is implanted during the operation within the left rectal muscle bed. After the operation is completed, the gastric restriction stoma can be modified by locating a reservoir injection port radioscopically and introducing a needle into the port to inflate or aspirate the inflatable member.

In yet another embodiment of this invention, not shown, the plication device is U-shaped and utilizes first and second inflatable members which are peripherally sealed and carried on the inner surface of the first and second legs, respectively as in the preferred embodiment; however, the device in this embodiment has a single fluid flow path to inflate the first and second inflatable members. The flow path consists of a conduit within the flexible latch member that communicates with reservoir 40, a first lumen that extends at least in part axially within the first leg, a bight lumen that extends laterally within the bight portion, and a second lumen extending axially within the second leg. The first and second inflatable members communicate with a respective inflation port and the inflation ports are in fluid communication with the first and second lumens. And as above described, the use of a silicone implanted reservoir 40 which is well known in the prior art permits inflation and aspiration of the first and second inflatable members. The gastric restriction stoma may be modified after the stomach is plicated and one of the flexible latch member serrations locked with respect to the first and second legs. As in the above described embodiments, reservoir 40 has an injection port that can be located radioscopically and accessed by a needle to supply or aspirate saline to inflate or aspirate the inflatable members.

While I have shown and described embodiments of a stomach plication device for morbid obesity surgery, it is to be understood that the invention is subject to many modifications without departing from the scope and spirit of the claims recited herein.

What is claimed is:

1. A fluid inflatable device to plicate the stomach for morbid obesity surgery, comprising:
    a) a frame comprising a first leg having a free end, a hinged end and an inner surface, a second leg having a free end, and a hinged end and an inner surface, and a bight portion interconnecting said hinged ends and said inner surfaces of said first and second legs, where at least one of said first and second legs is so hinged to said bight portion to permit rotation relative thereto;
    b) a first inflatable member sealingly attached to said inner surface of said first leg;
    c) a second inflatable member sealingly attached to said inner surface of said second leg;
    d) latch means carried by said first leg adjacent said free end for locking said first and second legs in substantially fixed spatial relationship; and
    e) fluid means carried by and extending at least in part within said latch means for supplying and aspirating fluid to selectively inflate or aspirate either said first or said second inflatable member or both said first and second inflatable members to plicate said stomach,
where said first leg has an axis of elongation and a first lumen extending at least in part axially therein and in fluid communication with said fluid means, where said first leg has a first inflation port communicating with said first inflation member and said first lumen to permit inflation of said first inflatable member or aspiration of fluid from said first inflatable member, and where said bight portion has bight lumen and said first leg has a third lumen extending at least in part axially therein and communicating with said bight lumen and said fluid means, said second leg having an axis of elongation and a second lumen extending at least in part axially therein and further having a second inflation port where said second lumen communicates with said bight lumen and said second inflation port to permit inflation of said second inflatable member or aspiration of fluid from said second inflatable member and where said latch means comprises a flexible latch member carried by said first leg, said flexible latch member having a first conduit and a second conduit where said first conduit is in fluid communication with said fluid means and said first lumen, and said second conduit is in fluid communication with said third lumen, and where said second leg has a latch cavity and said flexible latch member has at least one serration so dimensioned and proportioned such that said serration upon engagement with said latch cavity locks said first and second legs in substantially fixed spatial relationship.

2. The fluid inflatable device recited in claim 1 where said frame in U-shaped.

3. A fluid inflatable device to plicate the stomach for morbid obesity surgery, comprising:
   a) a first leg having an axis of elongation, a first free end, a hinged end, and a first inflation port, said first leg further having a first lumen extending at least in part axially therein and communicating with said first inflation port;
   b) a second leg having an axis of elongation, a second free end, a hinged end, and a second inflation port, said second leg further having a second lumen extending at least in part axially therein and communicating with said second inflation port, and an axially extending third lumen;
   c) a bight portion so connected to said hinged ends of said first and second legs to permit at least one said legs to articulate with respect to said bight portion and where said bight portion has a bight lumen therein communicating with said third lumen and said first lumen respectively;
   d) a first inflatable member sealingly carried by said first leg and extending at least in part axially therewith, where said first inflatable member communicates with said first inflation port;
   e) a second inflatable member sealingly carried by said second leg and extending at least in part axially therewith, where said second inflatable member communicates with said second inflation port;
   f) latch means carried by said first leg adjacent said free end of said first leg for selectively locking said first and second legs in pre-determined fixed lateral relationship, said latch means having a first conduit and a second conduit where said first conduit communicates with said second lumen and said second conduit communicates with said third lumen;
   g) fluid means carried by and extending at least in part within said latch means for selectively supplying fluid to said first conduit for inflating said first inflatable member to a pre-determined pressure and for aspirating said fluid to a selected pressure, and for selectively supplying said fluid to said second conduit for inflating said second inflatable member to a predetermined pressure and for aspirating said fluid to a selected pressure.

4. The fluid inflatable device recited in claim 3 when said latch means comprises a flexible latch member associated with said first free end of said first leg, said flexible latch member containing said first and second conduits and where said second leg has a latch cavity adjacent said second free end, said flexible latch member having at least one serration so dimensioned and proportioned such that said serration upon engagement with said latch cavity locks said first and second legs in substantially fixed lateral relationship.

5. The fluid inflatable device recited in claim 4 where said first leg, said second leg, and said bight portion form a U-shaped frame.

* * * * *